(12) United States Patent
Maschke

(10) Patent No.: US 8,257,375 B2
(45) Date of Patent: Sep. 4, 2012

(54) CATHETER AND MEDICAL APPARATUS AS WELL AS METHOD FOR ASSISTING AN INTERVENTION TO REMOVE PLAQUE

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 129 days.

(21) Appl. No.: 12/719,880

(22) Filed: Mar. 9, 2010

(65) Prior Publication Data

US 2010/0241147 A1 Sep. 23, 2010

(30) Foreign Application Priority Data

Mar. 23, 2009 (DE) .......................... 10 2009 014 489

(51) Int. Cl.
*A61B 17/22* (2006.01)
(52) U.S. Cl. ...................................... 606/159; 600/439
(58) Field of Classification Search .................. 606/159, 606/170, 180; 604/22, 84, 508; 600/439, 600/459
See application file for complete search history.

(56) References Cited

U.S. PATENT DOCUMENTS

| | | | |
|---|---|---|---|
| 5,042,486 A | 8/1991 | Ermert | |
| 6,299,622 B1 | 10/2001 | Snow et al. | |
| 6,377,048 B1 | 4/2002 | Alexandrowicz | |
| 6,600,319 B2 | 7/2003 | Golan | |
| 6,659,940 B2 | 12/2003 | Adler | |
| 6,714,484 B2 | 3/2004 | Ladabaum | |
| 7,087,023 B2 | 8/2006 | Daft | |
| 2003/0097048 A1 | 5/2003 | Bouma | |
| 2006/0103850 A1 | 5/2006 | Alphonse | |
| 2008/0058917 A1* | 3/2008 | Klingenbeck-Regn et al. | ............................ 623/1.11 |
| 2008/0065124 A1 | 3/2008 | Olson | |
| 2008/0065125 A1* | 3/2008 | Olson | ........................... 606/159 |

FOREIGN PATENT DOCUMENTS

| | | |
|---|---|---|
| DE | 19852467 A1 | 7/1999 |
| DE | 102004008371 A1 | 9/2005 |
| DE | 102004015639 A1 | 10/2005 |
| DE | 102004015641 B3 | 3/2006 |
| DE | 102005027951 A1 | 1/2007 |
| DE | 102005045373 A1 | 4/2007 |
| DE | 102005059271 A1 | 6/2007 |
| DE | 102006040936 A1 | 3/2008 |

(Continued)

OTHER PUBLICATIONS

A. Arena et al; Intercorporeal Videoprobe (IVP); Medical and Care Compunetics 2, L.Bos et al (Eds) IOS Press, 2005, p. 167 ff; Magazine; 2005.

(Continued)

*Primary Examiner* — Victor Nguyen

(57) ABSTRACT

A catheter for removing plaque in a blood vessel and a medical apparatus having a catheter of this kind are proposed. The catheter has a catheter sheath, a cutter for removing plaque disposed in the region of the distal end of the catheter sheath, a catheter tip disposed in the region of the distal end of the catheter sheath and bendable relative to the catheter sheath, and at least one imaging sensor arranged in the region of the distal end of the catheter sheath or in the bendable catheter tip. The image signals recorded by the catheter are transmitted for display purposes to an image processing and playback device. A method for assisting a minimally invasive intervention to remove plaque in a blood vessel by the catheter is also provided.

9 Claims, 5 Drawing Sheets

FOREIGN PATENT DOCUMENTS

WO            WO 0111409 A2     2/2001

OTHER PUBLICATIONS

H. Lim et al; Optical frequency domain imaging with a rapidly swept laser in the 815-870 nm range; Harvard Medical School and Wellman Center for Photomedicine, Massachusetts 02114; Magazine; 2006.

R.J. Dickinson, R.I. Kitney; Miniature ultrasonic probe construction for minimal access surgery; Department of Bioengineering, Imperial College, London; Institute of Physics Publishing; Physics in Medicine and Biology (Phys. Med.Biol. 49 (2004) 3527-3538.; London; 49; Magazine; 2004.

SilverHawk-R LS-C, The RockHawk,SilverHawk-R LS-C, Conquer calcium. Oct. 2007 ev3; Others; 2007.

Silverhawk Plaque Excision System ev3 Instructions for use, 70454-001 Rev. 05/08; Book.

* cited by examiner

CATHETER AND MEDICAL APPARATUS AS WELL AS METHOD FOR ASSISTING AN INTERVENTION TO REMOVE PLAQUE

CROSS REFERENCE TO RELATED APPLICATIONS

This application claims priority of German application No. 10 2009 014 489.7 filed Mar. 23, 2009, which is incorporated by reference herein in its entirety.

FIELD OF THE INVENTION

The invention relates to a catheter and a medical apparatus for removing plaque in a blood vessel of a patient. The invention also relates to a method for assisting a minimally invasive intervention to remove plaque in a blood vessel.

BACKGROUND OF THE INVENTION

Vascular diseases involving consequential complications such as heart attack or stroke are among the most common medical conditions having a fatal outcome. Heart attack is caused by a disease of the coronary vessels, wherein arteriosclerotic deposits, the plaque, promote local thrombus formation which can lead to a total blockage (occlusion) of coronary arteries and consequently to a blocking of the blood flow. In the majority of cases the occlusion is treated these days by means of what is teamed PCTA (Percutaneous Transluminal Coronary Angioplasty). Toward that end the constrictions in the coronary arteries are stretched with the aid of a balloon catheter. However, clinical studies have revealed that restenosis occurs in many patients after application of this method. The restenosis rate can be lowered through the insertion of a stent into a widened constriction.

In order to reduce the restenosis rate further, a procedure called DCA (Direct Coronary Atherectomy) can be performed which represents a method for recanalizing stenosed coronary arteries and is also referred to as "debulking". An atherectomy device used for this purpose comprises an atherectomy catheter having a metal housing in which there is contained what is termed a "cutter" for removing for removing plaque. The "cutter", which is a conically ground excising blade, is connected via a flexible link to a motor of the atherectomy device disposed outside of the atherectomy catheter, which motor drives the cutter at approx. 500 rpm. Atherectomy catheters of said kind are described for example in DE 10 2004 008 371 B4 and DE 10 2005 059 271 A1. In addition to a cutter for removing plaque the atherectomy catheters known from DE 10 2004 008 371 B4 and DE 10 2005 059 271 A1 also have in each case an OCT sensor (OCT: Optical Coherence Tomography) or an OCT sensor and an IVUS sensor (IVUS: Intravascular Ultrasound) by means of which in each case image information relating to plaque and vascular walls, e.g. inflammatory processes, can be acquired which is important for an operation to remove the plaque. In particular the vascular section "blocked" in each case can be detected and the removal of the plaque controlled and monitored during and after the medical intervention.

A drawback with said atherectomy catheters is that they have an inflexible stationary tip. This can easily result in an injury to a vascular wall. Furthermore, tightly curved or narrow vascular sections cannot be reached with the atherectomy catheter due to the inflexible tip.

SUMMARY OF THE INVENTION

The object underlying the invention is therefore to disclose a catheter, a medical apparatus and a method of the kind cited in the introduction in such a way that plaque in a blood vessel can ideally be removed in an improved way.

This object is achieved according to the invention by means of a catheter for removing plaque in a blood vessel, the catheter having a catheter sheath enclosing a catheter cavity, a cutter disposed in the region of the distal end of the catheter sheath for the purpose of removing plaque, a catheter tip disposed in the region of the distal end of the catheter sheath and bendable relative to the catheter sheath, and at least one imaging sensor arranged in the region of the distal end of the catheter sheath or in the bendable catheter tip.

With the aid of the bendable catheter tip it is also possible to reach tightly curved or narrow vascular sections of a blood vessel with the catheter for the purpose of removing plaque. Furthermore, image information relating to the plaque or the inside of the blood vessel can be recorded by means of the at least one imaging sensor and used for manipulating the catheter during the removal of the plaque. In particular the acquisition of image information by means of the imaging sensor permits the X-ray fluoroscopy used per se for handling, positioning and controlling or monitoring the orientation of the catheter to be dispensed with as far as possible, which X-ray fluoroscopy exposes not only a patient, but also the medical staff carrying out an intervention to remove plaque to harmful radiation.

A further aggravating factor in the use of X-ray fluoroscopy images is that the catheter and/or the local environment of the catheter inside the body are relatively poorly visible. Although the immediate environment of the catheter tip can be visualized more clearly and with higher contrast by injecting contrast agents, there are also patients who have an allergic reaction to contrast agents, which can subsequently lead to dangerous complications. Furthermore, the blood vessels, in particular the coronary vessels, are only represented two-dimensionally. Consequently the medical staff are often unable to differentiate exactly between plaque and vascular wall. This is associated with additional risks for the patient, for if too little plaque is removed, the desired blood flow cannot be restored and there is a danger of restenosis; if, on the other hand, too much tissue is removed, this can result in a perforation of the vessel.

In order to avoid difficulties of this kind the at least one imaging sensor is therefore arranged in the region of the distal end of the catheter sheath or in the bendable catheter tip. This permits a comparatively precise, high-resolution visualization of the spatial environment of the cutter. By means of the imaging sensor "live images" from the site of the minimally invasive intervention, i.e. directly from the blood vessel, can be transmitted to an externally disposed image processing and playback device, e.g. a computer-controlled visualization system with attached visual display unit. The introduction and advancement of the catheter into and through the blood vessel or blood vessels and the precisely targeted positioning of the catheter can be tracked in realtime for monitoring and control purposes. A high-resolution visualization of the catheter's location made possible in this way enables fine positional corrections of the catheters to be made in near-realtime.

If necessary X-ray photographs for monitoring purposes can also be taken at chosen points in time to supplement the imaging with the aid of the catheters.

According to a variant of the invention the at least one imaging sensor is configured and/or aligned in such a way that its image recording range at least partially covers a spatial area located around the distal end of the catheter sheath or around the bendable catheter tip. In other words, referred to the catheter sheath arranged approximately cylindrically around a central axis, the at least one imaging sensor "looks" substantially radially outward.

According to another variant of the invention the at least one imaging sensor is configured and/or aligned in such a way that its image recording range at least partially covers the spatial area located in front of the distal end of the catheter sheath or the spatial area located in front of the catheter tip. Referred to the advancement of the catheter, therefore, the imaging sensor "looks" to the front, which is beneficial for monitoring the advancement of the catheter and its positioning.

Ideally the two aforesaid possibilities are suitably combined with one another for the at least one imaging sensor, such that the sensor has the largest possible image recording range both in the radial and in the forward direction. Alternatively, provided space conditions permit, a plurality of imaging sensors can also be provided which cover different solid angle ranges in mutually complementary fashion.

According to an embodiment variant of the invention the at least one imaging sensor is longitudinally displaceable with respect to the catheter sheath or with respect to the bendable catheter tip. It can be provided, for example, to move the at least one imaging sensor from a "retracted" stop position in the region of the distal end of the catheter sheath or, as the case may be, from a "retracted" stop position in the bendable catheter tip in the forward direction out of the catheter sheath or the catheter tip in order thereby to define, with the catheter sheath or catheter tip maintained in a constantly held position, a variably positionable observation point from which the regions located further forward can be inspected. For this purpose the imaging sensor can be disposed for example on an inner catheter which is displaceable relative to the outer catheter sheath or relative to the catheter tip and arranged in the catheter cavity or on an internal part.

According to variants of the invention the at least one imaging sensor is implemented as an (acoustic) ultrasound sensor, as a magnetic resonance sensor or as an optical image sensor, in particular as a CMOS image sensor, OCT image sensor, LCI image sensor, NIR image sensor or as an OFDI image sensor.

Imaging by means of ultrasound (sonography) is performed according to what is called the pulse-echo method. An electrical pulse from a radio-frequency generator is converted in the sound head of an ultrasound transducer (mostly a piezoelectric crystal, though a silicon-based sensor is also possible) into a sound pulse and emitted. The sound wave is partially or completely scattered or reflected by the inhomogeneities of the tissue structure. A returning echo is converted into an electrical signal in the sound head and subsequently visualized in an attached electronic analysis and display unit, wherein a 2D or 3D scan of the examination region can be performed by swiveling the sensor with the aid of mechanical or electronic means. Intravascular ultrasound (IVUS) imaging is particularly suitable for imaging deeper-lying tissue layers and vascular structures.

However, the imaging sensor can also be what is termed an IVMRI sensor for intravascular magnetic resonance tomography (IVMRI=Intra Vascular Magnetic Resonance Imaging). In magnetic (nuclear) resonance tomography, the magnetic moments (nuclear spins) of the atomic nuclei of the tissue being examined are aligned in an external magnetic field and excited into a gyratory motion (precession) by means of irradiated radio waves, with an electrical magnetic resonance signal being induced as a result of relaxation processes in an associated receiving coil, said signal constituting the basis for the calculation of the image.

The elements generating the magnetic field as well as the transmitting and receiving coils have recently been successfully miniaturized and integrated in an imaging IVMRI sensor in such a way that an intracorporal or, as the case may be, intravascular application of the MRI method (MRI=Magnetic Resonance Imaging) is possible wherein the requisite static magnetic field is advantageously generated or, as the case may be, applied inside the patient's body. A concept of this kind is described e.g. in U.S. Pat. No. 6,600,319.

For this purpose a permanent magnet or an electromagnet for generating a static magnetic field and a coil acting equally as a transmitting and as a receiving coil are integrated into the IVMRI sensor. The magnet generates field gradients of preferably 2 T/m to 150 T/m in the vicinity of the vessel or organ that is to be examined. In the vicinity, in the present context, means at a distance of up to 20 mm away from the magnet. Depending on the strength of the magnetic field, radio waves in the frequency range from 2 MHz to 250 MHz can be coupled out via the coil for the purpose of exciting the surrounding body tissue. Higher static magnetic field strengths require higher frequencies for the excitation field. The coil advantageously serves also for receiving the associated "response field" from the body tissue. In an alternative embodiment separate transmitting and receiving coils can be provided.

In contrast to conventional MRI systems, the IVMRI sensor and the electronic circuitry and digital analysis units provided for signal conditioning and analysis are advantageously configured in such a way that they can also operate with high local field gradients even in the case of a comparatively inhomogeneous magnetic field and generate corresponding magnetic resonance images. Since under these conditions the received echo signals are influenced in a characteristic manner by the microscopic diffusion of water molecules in the examined tissue, it is usually made possible to achieve an excellent visualization and differentiation between different soft parts, e.g. between lipid layers and fibrous tissue. This is of particular relevance, especially in the now provided application area of minimally invasive interventions. From more recent investigations it is known, namely, that the typical infarction regions in the heart in particular can be visualized very well by means of MRI.

As an alternative to the concept described here, the static magnetic field can also be generated by means of external magnets. In contrast to conventional MRI, however, the dynamic fields, i.e. the radio waves, are beneficially generated intravascularly in the case of this embodiment variant also, i.e. by means of a number of transmitting and receiving units disposed on the catheter device.

In an alternative or additional embodiment an optical imaging sensor can also be provided. For example, an optical semiconductor detector based on the well-known CMOS technology (CMOS=Complementary Metal Oxide Semiconductor) can be considered as a suitable choice for detecting incident light. Like the CCD sensors (CCD=Charge-Coupled Device) known mainly from the field of digital photography, a CMOS sensor of the aforesaid type, also known as an "active pixel sensor", is based on the internal photoelectric effect and as well as having a low current consumption also possesses the advantage that it is particularly cheap to manufacture. With this imaging variant, a suitable light source, e.g. an LED (LED=Light Emitting Diode), must be provided in the region of the catheter tip for the purpose of illuminating the examination and treatment region, which light source can be supplied with electric current via an electrical lead routed through the catheter cavity.

In a further embodiment variant the catheter can also be equipped with an OCT sensor (OCT=Optical Coherence Tomography).

Optical coherence tomography imaging delivers high-resolution images which comparatively accurately reproduce in particular the structures close to the vessel surface. The principle of this method is based on the fact that light, preferably infrared light, supplied by the catheter via a fiber-optic light guide is beamed into the vessel or onto a tissue structure, the light reflected therefrom being coupled back again into the fiber-optic light guide and routed to an analysis apparatus. In the analysis unit—as in the case of a Michelson interferometer—the interference of the reflected light with the reference light is analyzed in order to generate the image.

Whereas conventional interferometric equipment preferably operates with laser light of a defined wavelength, which light possesses a comparatively great optical coherence length, in the case of what is termed LCI (LCI=Low Coherence Interferometry), light sources having broadband radiation characteristics ("white light") and having a comparatively low coherence length of the emitted light are used. Corresponding image sensors which are now provided according to an advantageous embodiment of the invention for use in the catheter are described for example in US 2006/0103850 A1.

In a further modification an image sensor can also be provided which is based on the so-called OFDI principle (OFDI=Optical Frequency Domain Imaging). This method is related to OCT, but uses a wider frequency band. The operating principle is described in more detail e.g. in the publication "Optical frequency domain imaging with a rapidly swept laser in the 815-870 nm range", H. Lim et al., Optics Express 5937, Vol. 14, No. 13.

Finally, the catheter can also have an imaging sensor which is based on what is termed "near-infrared (NIR) diffuse reflectance spectroscopy".

Moreover, combinations of at least two optical sensors of the aforementioned type can also be present.

A tabular overview summarizes the strengths and weaknesses of the respective optical imaging methods (from ++= particularly good or suitable, to −−=deficient or unsuitable):

| Comparison of the image sensors | Near resolution | Far resolution | Penetration of blood |
|---|---|---|---|
| Optical (CMOS) | + | + | − |
| OCT | ++ | − | −− |
| LCI | + | + | + |
| NIR | − | − | +/− |
| OFDI | ++ | − | + |

Since the solid angle detectable or, as the case may be, to be monitored by means of the respective image sensor is usually limited, it is advantageous in particular in the case of the already mentioned configuration with radial line of sight (in relation to the central axis of the catheter device) if, according to a variant of the invention, the imaging sensor can be rotated relative to the catheter sheath by way of a driveshaft routed in the catheter cavity. By this means it is possible to obtain a 360° panoramic view without the need to rotate the catheter sheath itself relative to the environment inside the body.

Alternatively it is also conceivable to dispose a plurality of imaging sensors in a distributed arrangement around the circumference of the catheter sheath and preferably looking outward and to provide a cyclical data readout from the sensors, e.g. via a multiplexer. Such a configuration is implemented for example by arranging the sensors in a stationary position on/at the catheter sheath. Alternatively (or in addition) thereto the sensors (or additional sensors) can also be arranged in a group inside the catheter sheath. Advantageously they are longitudinally displaceable, where appropriate as a sensor cluster or separately. With a configuration such as this only a single signal line is required inside the catheter sheath, via which signal line the image data of the different sensors is sent or, as the case may be, polled sequentially in the manner of a serial interface. A small number of signal lines, preferably only a single one, limits the amount of space required inside the catheter sheath and is therefore of advantage in terms of the ability to make use of the mechanical flexibility and pliability of the catheter sheath.

By (mechanical or electronic) rotation of the image sensor with simultaneous retraction or advancing it is advantageously possible to generate 3D images or, as the case may be, volume datasets by means of suitable signal conditioning and image calculation methods known in principle from the prior art.

In an advantageous development at least one position sensor is arranged in the region of the distal end of the catheter sheath or in the catheter tip in order to enable the current position and preferably also the orientation of the catheter sheath or catheter tip to be determined. Typically, the position sensor comprises a number of electromagnetic transmitting coils which interact with a number of externally disposed receiving coils or signal detectors, i.e. provided outside of the patient.

In an alternative embodiment the roles of the transmitting and receiving units can also be reversed, i.e. the receiving coils are fixed on the catheter side, while the transmitting coils are preferably disposed in a stationary position in space.

In a further beneficial embodiment at least one passive sensor, an RFID transponder (RFID=Radio Frequency Identification) for example, is fixed on the catheter side. A signal transmitted by a stationary transmitting coil causes a response signal to be induced in the RFID transponder, which signal is received by a stationary receiving coil and permits precise spatial localization of the RFID transponder. A passive sensor therefore needs no external energy supply, and consequently—advantageously—no external supply line.

Ultrasound sensors belonging to a position detection system based on ultrasound waves can also be used as position sensors as a substitute for electromagnetic position sensors. A position detection system of this type and its principle of operation are described in DE 198 52 467 A1, the disclosure of which in this regard is to be incorporated by reference into the present patent application. In this case there need to be provided an ultrasound transducer on the atherectomy catheter as well as four or more reference ultrasound transducers, preferably disposed outside the body of the patient P, in order to enable the position and orientation of the atherectomy catheter to be determined from distance measurements.

The position data received from the position sensor firstly facilitates the reliable introduction of the catheter and its navigation to the target region; secondly, said information advantageously supports the construction of three-dimensional images from a plurality of two-dimensional cross-sectional images. Furthermore, the position data can advantageously be incorporated into the computational correction of motion artifacts and the like.

In a further beneficial embodiment of the invention at least one magnetic element can be provided in the region of the catheter tip for the purpose of guiding the catheter by means of an external magnetic field. With this magnetic navigation, as it is called, the catheter is controlled and driven by means of an external magnetic field. The respective magnetic element can be a permanent magnet or an electromagnet.

As an alternative to the guiding of the catheter device by means of an external magnetic field, a mechanical means of navigation can be provided. For that purpose suitable mechanical elements, e.g. in the form of pull wires and the like, are beneficially integrated into the catheter device, which mechanical elements permit a temporary mechanical deformation, extension and/or deflection of the catheter or of individual, selectable catheter sections, in particular the catheter tip, by means of external tensile and compressive forces. The mechanical and/or magnetic guiding of the catheter device is preferably performed automatically with the aid of a computer-based control and drive device.

It can additionally be provided to introduce the catheter for removing plaque and lead it through an outer guide catheter into the vessel that is to be treated.

The object underlying the invention is also achieved by means of a medical apparatus for removing plaque in a blood vessel, the apparatus having a catheter as described hereintofore and an image processing and playback device, wherein the at least one imaging sensor of the catheter is connected via at least one signal line routed in the catheter cavity to the image processing and playback device disposed outside the catheter and wherein image information recorded by means of the at least one imaging sensor can be transmitted in realtime to said image processing and playback device.

The object underlying the invention is furthermore achieved by means of a method for assisting a minimally invasive intervention to remove plaque in a blood vessel by means of a catheter as described hereintofore, wherein image information is recorded in the blood vessel by means of the at least one imaging sensor of the catheter and transmitted in realtime to an image processing and playback device disposed outside the patient's body so that it can be displayed. The advancement of the catheter can be monitored and/or the orientation of the catheter controlled with the aid of the image information transmitted in realtime to the image processing and playback device.

A beneficial workflow for the deployment of the catheter for removing plaque and having integrated imaging looks for example as follows:
1. Positioning the patient on the treatment table
2. Possible preparatory X-ray examination
3. Introduction of the catheter via a venous access port
4. Guiding of the catheter based on the integrated imaging to the site of the plaque that is to be removed
5. Withdrawal and ablation of the plaque
6. Removal of the catheter
7. Possible monitoring by means of the imaging sensor to check whether the plaque has been completely removed
8. Possible concluding X-ray examination as supplementary check
9. Transfer of the patient.

BRIEF DESCRIPTION OF THE DRAWINGS

Exemplary embodiments of the invention are illustrated in the attached simplified schematic drawings, in which.

DETAILED DESCRIPTION OF THE INVENTION

Parts or components of the inventive catheter and of the inventive medical apparatus which are at least substantially identical in terms of design and function are labeled with the same reference signs in all the figures.

Figure 1:
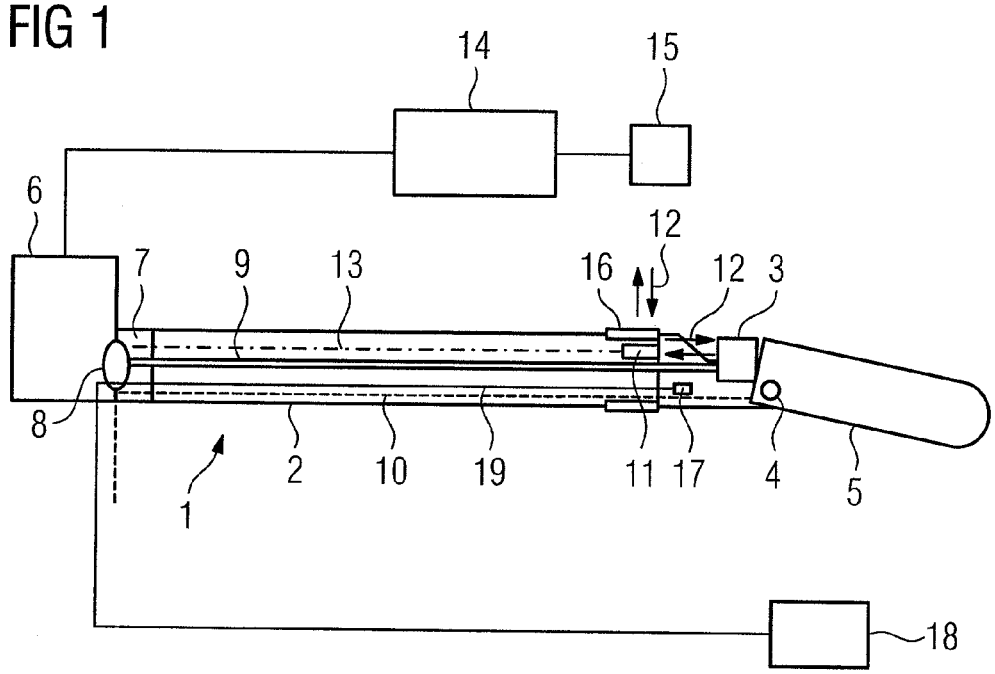
FIG. 1 shows a medical apparatus having a catheter for removing plaque which is depicted in longitudinal section and has an imaging sensor in the distal end of the catheter sheath.

The inventive catheter 1 shown in FIG. 1 is provided to allow a minimally invasive intervention for the purpose of removing plaque in coronary vessels and is also referred to as an atherectomy catheter. In the case of the present exemplary embodiment of the invention the catheter 1 is preferably a "SILVERHAWK®" catheter, as described in US 2008/0065124 A1 and in "SILVERHAWK Plaque Excision System", ev3, Instructions for use, page 1-2, 70454-001 Rev. 05/08 (see also http://www.ev3.net/).

In the case of the present exemplary embodiment of the invention the catheter 1 comprises a catheter sheath 2 at the distal end of which is disposed an excision blade 3 for removing plaque, said blade also being referred to as a "cutter". At its distal end the catheter sheath 2 also has a catheter tip 5 which is bendable with the aid of an articulated joint 4.

The proximal end of the catheter 1 is connected to a unit 6 which serves as a signal interface and has at least one drive unit (not show explicitly). The connection of the catheter 1 to the unit 6 is effected via a mechanical/electrical connection unit 7 which has at least one rotary coupling 8 for terminations. Thus the cutter 3 is connected to the drive unit of the unit 6 via a driveshaft 9 running through the cavity of the catheter sheath 2 and the rotary coupling 8, such that the cutter 3 can be placed into rotation in order to remove plaque.

The bendable catheter tip 5 is connected to a control terminal (not shown in further detail) via a line 10 running through the cavity of the catheter sheath 2 and the connection unit 7 to allow targeting bending of the catheter tip 5.

Figure 2:
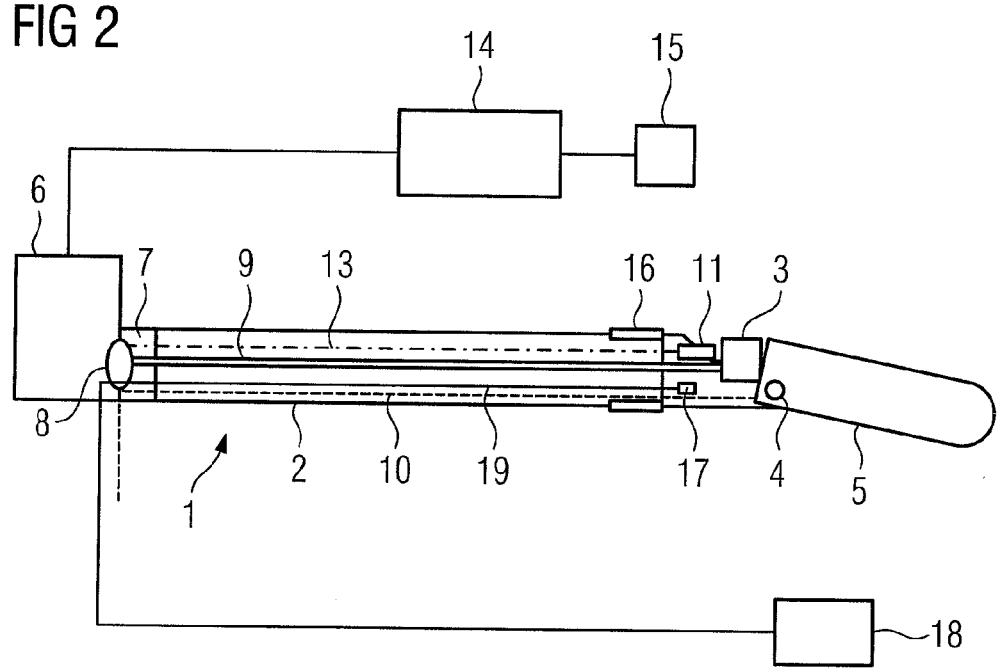
FIG. 2 shows the catheter from FIG. 1 with longitudinally displaced imaging sensor.

In contrast to the known "SILVERHAWK®" catheter, the inventive catheter 1 in the distal end of the catheter sheath 2 has an imaging sensor 11 which in the case of the present exemplary embodiment of the invention is disposed behind the cutter 3 inside the catheter sheath 2 and is longitudinally displaceable relative to the catheter sheath 2. FIG. 2 shows the imaging sensor 11 in a longitudinally displaced position. Depending on sensor type and other details of the embodiment, the image recording range of the imaging sensor 11 is preferably directed radially outward (toward the surrounding vascular wall, not shown here) and/or in the forward direction (i.e. in the advancement direction of the catheter 1), as indicated symbolically by means of the arrows 12.

The imaging sensor 11 can be for example an optical sensor, an acoustic (ultrasound) sensor or a sensor based on the magnetic resonance principle. The signal and supply lines 13 necessary for its operation and for transmitting the recorded image data are routed in the interior of the catheter sheath 2 up to the connection unit 7. The connection unit 7 is connected via the aforesaid signal interface to an external image processing and playback device 14, to which the image information recorded by means of the imaging sensor 11 is transmitted for processing and playback on a visual display device 15. In this way image information recorded intravascularly or intracorporally by the imaging sensor 11 can be presented, possibly also only after having first been computationally processed, as "live images" from the treatment site on the visual display device 15.

In order to enable the imaging sensor 11 to be rotated about its own axis inside the catheter sheath 2 and relative to the catheter sheath 2, a rotatable driveshaft can also be disposed in the cavity of the catheter sheath 2, though said driveshaft is not shown in further detail in FIG. 1. In this arrangement, in contrast to the layout shown in FIGS. 1 and 2, the driveshaft and the imaging sensor 11 can also be disposed centrally, i.e. substantially on the central axis of the catheter 1. In particular when interferometric imaging methods are used, fiber-optic light guides can also be routed in the catheter sheath 2 and incident and emergent light beams can be guided via said light guides to an externally installed interferometer unit or the like which can be connected via the rotary coupling 8. In the region of the imaging sensor 11 the inner protective sheath and/or the catheter sheath 2 have/has a transparent window 16, possibly also an optical lens, for the respective imaging method.

In addition, one or more lines (not shown here) can (optionally) be provided for a flushing fluid or a contrast agent which can be injected into the blood vessel that is to be treated via an outlet aperture disposed close to the imaging sensor 11 at the distal end of the catheter sheath 2.

Finally, at least one electromagnetic position sensor 17 can be provided in the region of the distal end of the catheter sheath 2 in addition to the imaging sensor 11, which position sensor 17, operating on the transmitter-receiver principle in cooperation with an electromagnetic position detection unit 18 disposed outside the patient's body, enables a precise pinpointing/localization of the distal end of the catheter sheath 2 by identifying the coordinates of the catheter sheath 2. The position data thus acquired can be supplied to the image processing and playback device 14, for example, and taken into account during the image reconstruction, specifically in the course of artifact correction. The necessary signal lines 19 for the position sensor 17 run through the cavity of the catheter sheath 2 and the rotary coupling 8 to the position detection unit 18.

Figure 3:
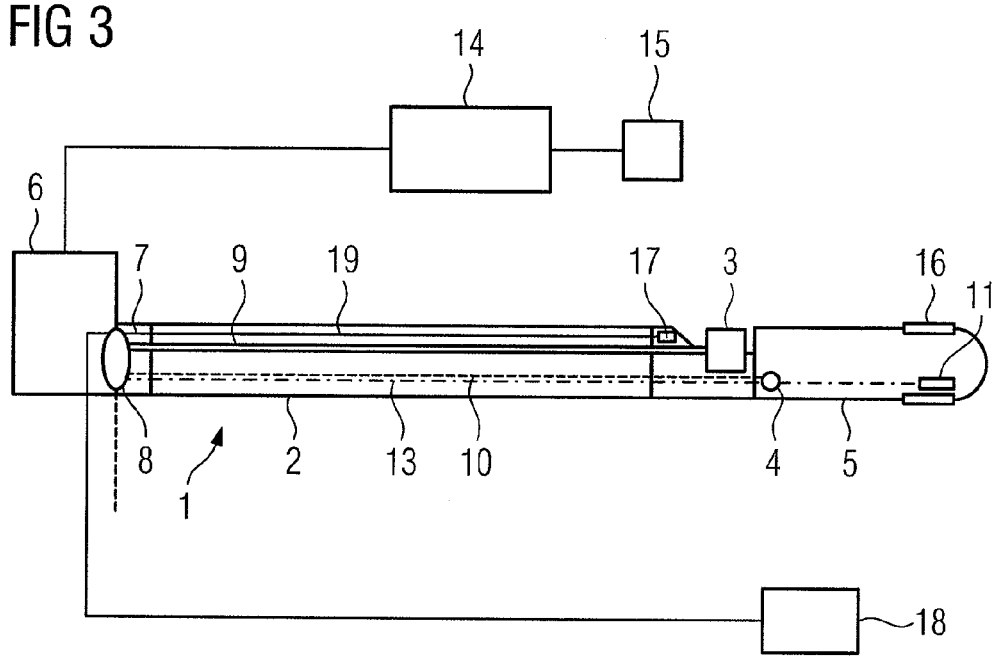
FIG. 3 shows a medical apparatus having a catheter for removing plaque which is depicted in longitudinal section and has an imaging sensor in the bendable catheter tip.
Figure 4:
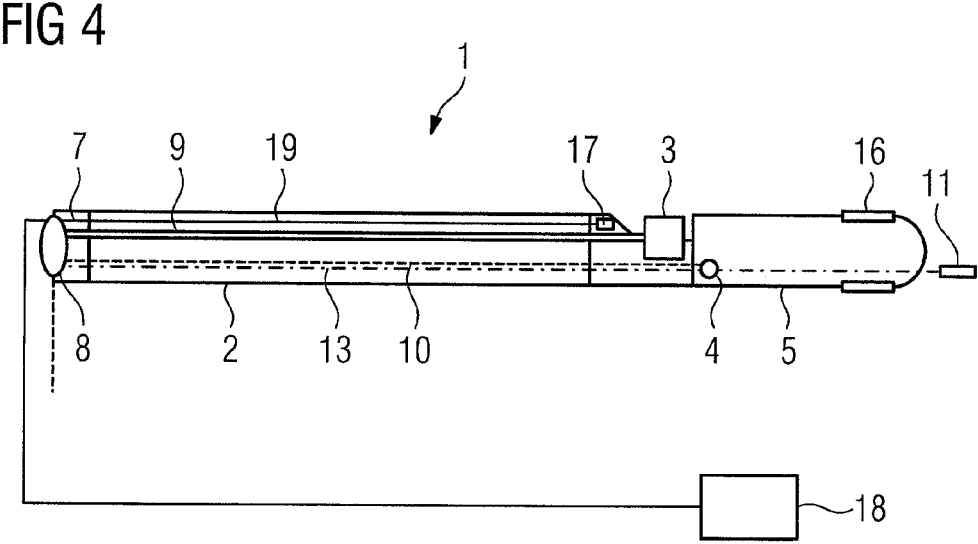
FIG. 4 shows the catheter from FIG. 3 with longitudinally displaced imaging sensor.

FIGS. 3 and 4 illustrate a structural modification of the catheter 1.

In the case of the catheter 1 shown in FIGS. 3 and 4 the imaging sensor 11 is arranged, not in the distal end of the catheter sheath 2, but in the bendable catheter tip 5, which is also provided with a corresponding ring-shaped transparent window 16. The imaging sensor 11 is mounted so as to be longitudinally displaceable in the catheter tip 5 and accordingly can be pushed out of the catheter tip 5, as shown in FIG. 4, for the purpose of recording image information.

Figure 5:
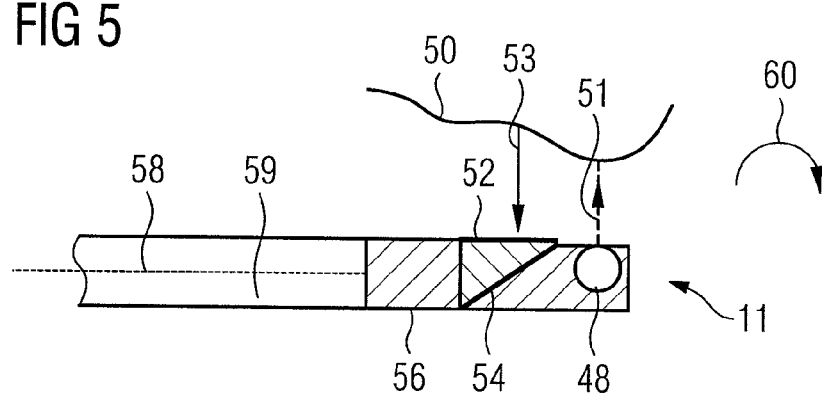
FIG. 5 shows a detail view of an optical sensor having a lateral/radial observation direction.

FIGS. 5-10 also depict various imaging sensors 11 which can be used in the catheter 1. FIG. 5 shows a CMOS-based optical sensor. A light source 48, in this case a high-performance micro-LED, illuminates the vascular wall 50 surrounding the catheter 1 and specifically the imaging sensor 11 approximately in a ring shape (emitted light 51). Light 53 reflected off the vascular wall 50 falls through a lens 52 onto a reflection mirror 54 (or also e.g. onto a prism with an analogous operating principle or beam guidance) and from there onto the actual CMOS image detector 56. The arrangement according to FIG. 5 is therefore configured for a radial line of sight (referred to the central axis 58 of the catheter 1). The full lateral 360° field of vision can be covered by means of a rotational movement around the central axis 58, indicated by the arrow 60, effected with the aid of the driveshaft 59.

Figure 6:
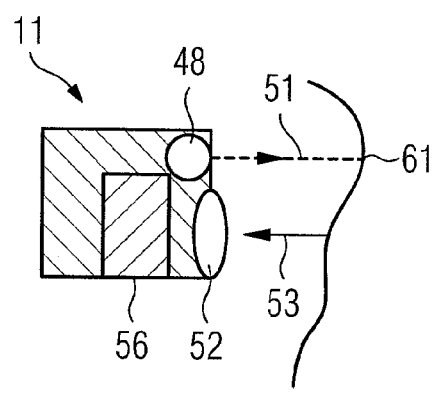
FIG. 6 shows a detail view of an optical sensor having a forward-directed observation direction.

Alternatively, FIG. 6 shows an example of a configuration of light source 48, lens 52 and CMOS image detector 56 by means of which a forward-directed observation is made possible which is particularly useful when advancing the catheter 1 through the blood vessels. An obstacle 61 lying in the forward direction and possibly impeding further advancement can be detected in this way. The two variants according to FIG. 5 and FIG. 6 can also be combined with each other where appropriate in order to provide a particularly extensive field of view or, as the case may be, image recording field in practically all directions.

Figure 7:
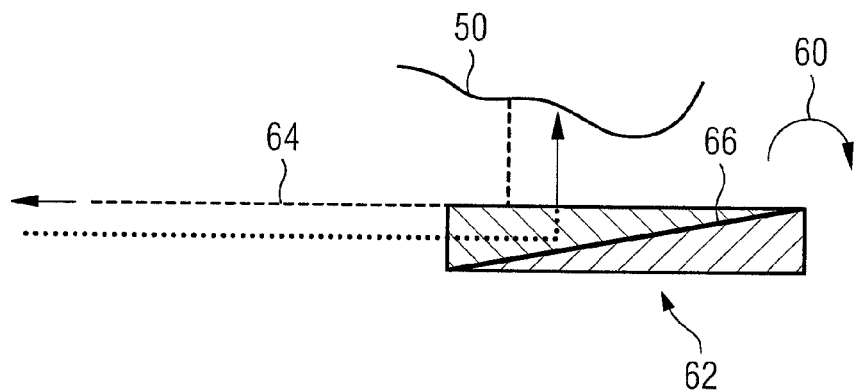
FIG. 7 shows a detail view of a sensor head for OCT or LCI imaging having a lateral/radial observation direction.
Figure 8:
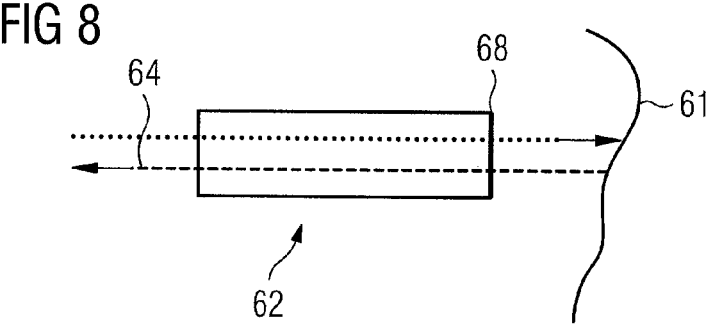
FIG. 8 shows a detail view of a sensor head for OCT or LCI imaging having a forward-directed observation direction.

The aforementioned observation directions, namely radial/lateral and forward-directed, can also be realized with other sensor types. For example, a configuration of an OCT or LCI sensor head 62 for radial radiation and radial reception is shown in FIG. 7, and a similar configuration for forward-directed radiation and reception is shown in FIG. 8. To put it more precisely, the reference sign 62 denotes only the sensor part or sensor head responsible for coupling the light into and out of the fiber-optic light guide 64; the actual interferometric analysis and image generation take place outside of the catheter 1. Shown in each case is the optical path of coupled-out and reflected light beams influenced by the reflection mirror 66 and the lens 68.

An IVMRI sensor or IVUS sensor can also be configured in a similar manner.

Figure 9:
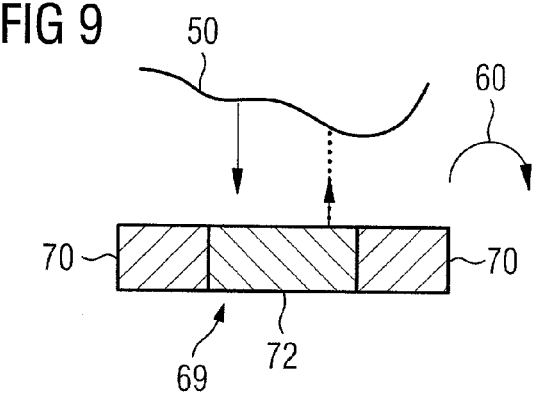
FIG. 9 shows a detail view of a sensor for IVMRI imaging having a lateral/radial observation direction.
Figure 10:
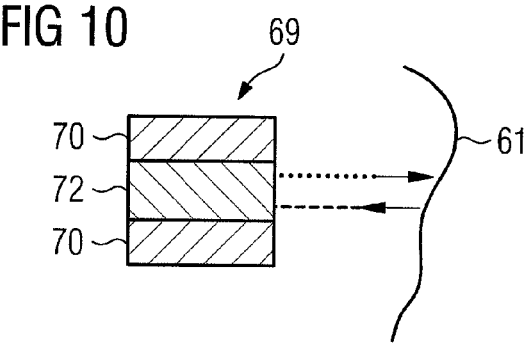
FIG. 10 shows a detail view of a sensor head for IVMRI imaging having a forward-directed observation direction.

FIG. 9 and FIG. 10 show schematic views of IVMRI sensors 69 having permanent magnets 70 for the static magnetic field and transmitting/receiving coils 72. The IVMRI sensor 69 shown in FIG. 9 is configured for radial recordings of image data and the IVMRI sensor 69 shown in FIG. 10 is configured for forward-directed recordings of image data.

If the imaging sensor 11 is a magnetic resonance sensor, the individual sensors of the blood pump 1, such as the magnetic resonance sensor and the position sensor 17 for example, are preferably read out with a time offset in a clocked manner, or alternatively the individual sensors are active with a time offset, in order to avoid a reciprocal interference as far as possible.

Figure 11:
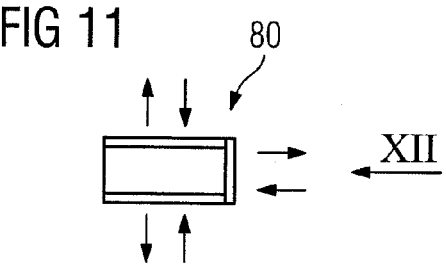
FIG. 11 shows a detail view of an IVUS sensor having a lateral/radial and forward-directed observation direction.

FIG. 11 shows an IVUS sensor 80 for radial and forward-directed radiation and corresponding reception of ultrasound waves. Instead of a single, possibly rotating, ultrasound sensor, an array of ultrasound sensor elements having different "lines of sight" can be provided both for radial and/or lateral radiation and corresponding reception of ultrasound waves and for forward-directed radiation and corresponding reception of ultrasound waves, said sensor elements being activated, i.e. excited and interrogated, for example cyclically via a multiplexer. For radial and/or lateral radiation and reception of ultrasound waves the ultrasound sensor elements can be arranged in a ring shape.

Figure 12:
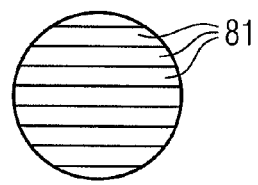
FIG. 12 shows the view in the direction of the arrow XII from FIG. 11
Figure 13:
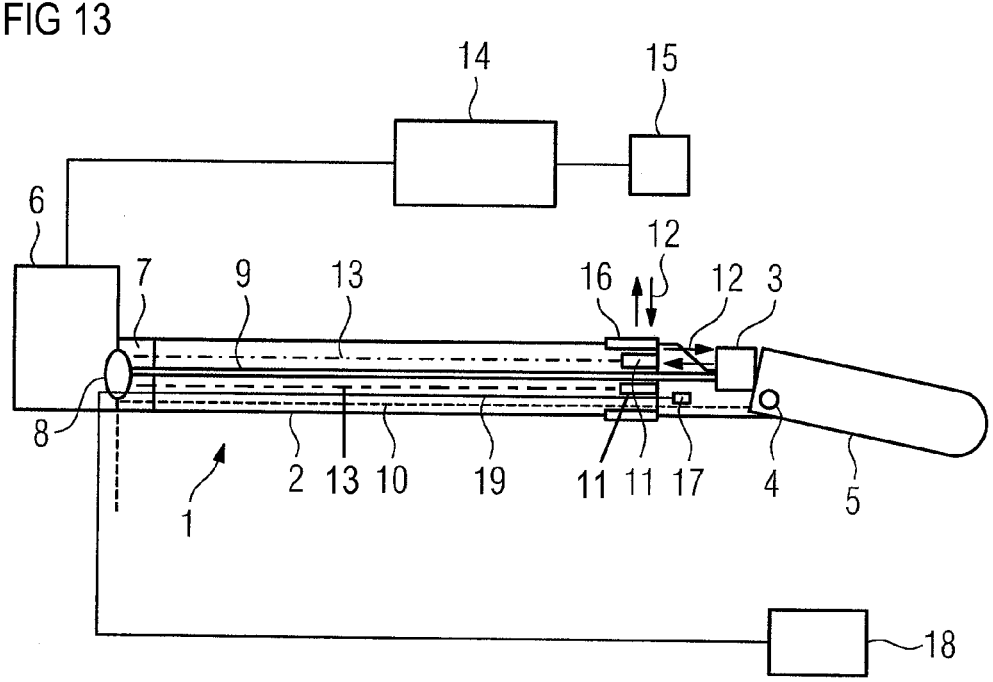
FIG. 13 shows the catheter from FIG. 1 with a plurality of imaging sensors disposed around the circumference of the catheter sheath.

FIG. 12 shows the view in the direction of the arrow XII from FIG. 11. FIG. 12 depicts a row-shaped arrangement of ultrasound sensor elements 81 for forward-directed radiation and corresponding reception of ultrasound waves, said sensor elements being activated, i.e. excited and interrogated, cyclically with the aid of a multiplexer.

The invention claimed is:

1. A catheter for removing a plaque in a blood vessel, comprising:
   a catheter sheath enclosing a catheter cavity;
   a cutter disposed in a region of a distal end of the catheter sheath that removes the plaque;
   a catheter tip disposed in the region of the distal end of the catheter sheath and bendable relative to the catheter sheath; and
   an imaging sensor arranged in the region of the distal end of the catheter sheath or in the bendable catheter tip that records an image of the plaque,
   wherein a plurality of imaging sensors are disposed around a circumference of the catheter sheath, and
   wherein the imaging sensors are cyclically activated via a multiplexer so that image data of the imaging sensors is sequentially readout.

2. The catheter as claimed in claim 1, wherein the imaging sensor is aligned for recording the image that partially covers a spatial area around the distal end of the catheter sheath or around the bendable catheter tip.

3. The catheter as claimed in claim 1, wherein the imaging sensor is aligned for recording the image that partially covers a spatial area in front of the distal end of the catheter sheath or in front of the catheter tip.

4. The catheter as claimed in claim 1, wherein the imaging sensor is longitudinally displaceable with respect to the catheter sheath or to the bendable catheter tip.

5. The catheter as claimed in claim 1, wherein the imaging sensor is selected from the group consisting of: an ultrasound sensor, a magnetic resonance sensor, an optical image sensor, a Complementary Metal Oxide Semiconductor image sensor, an Optical Coherence Tomography image sensor, an Low Coherence Interferometry image sensor, an near-infrared image sensor, and an Optical Frequency Domain Imaging image sensor.

6. The catheter as claimed in claim 1, further comprising a driveshaft routed in the catheter cavity that rotates the imaging sensor relative to the catheter sheath.

7. A medical apparatus for removing a plaque in a blood vessel, comprising:
   a catheter comprising:
      a catheter sheath enclosing a catheter cavity;
      a cutter disposed in a region of a distal end of the catheter sheath that removes the plaque;
      a catheter tip disposed in the region of the distal end of the catheter sheath and bendable relative to the catheter sheath; and
      an imaging sensor arranged in the region of the distal end of the catheter sheath or in the bendable catheter tip that records an image of the plaque; and
   an image processing and playback device disposed outside the catheter and connected to the imaging sensor that processes the image transmitted in realtime to the image processing and playback device,
   wherein a plurality of imaging sensors are disposed around a circumference of the catheter sheath, and
   wherein the imaging sensors are cyclically activated via a multiplexer so that image data of the imaging sensors is sequentially readout.

8. The medical apparatus as claimed in claim 7, wherein the image processing and playback device is connected to the imaging sensor via a signal line routed in the catheter cavity.

9. A method for a minimally invasive intervention to remove a plaque in a blood vessel by a catheter, comprising:
   recording an image of the plaque by an imaging sensor arranged in a region of a distal end of a catheter sheath of the catheter or in a bendable catheter tip of the catheter;
   transmitting the image in realtime to an image processing and playback device disposed outside the catheter;
   processing the transmitted image by the image processing and playback device; and
   displaying the processed image by a display device,
   wherein a plurality of imaging sensors are disposed around a circumference of the catheter sheath, and
   wherein the imaging sensors are cyclically activated via a multiplexer so that image data of the imaging sensors is sequentially readout.

* * * * *